United States Patent [19]

Schweizer et al.

[11] 3,977,790
[45] Aug. 31, 1976

[54] APPARATUS FOR MEASURING THE DENSITY OF A CONTAINED LIQUID, BY UTILIZING THE ANGULAR DISPLACEMENT OF THE LIMITING ANGLE AT TOTAL REFLECTION

[75] Inventors: Walter Schweizer; Martin-Ulrich ReiBland, both of Berlin, Germany

[73] Assignee: VDO Adolf Schindling, AG, Frankfurt am Main, Germany

[22] Filed: Sept. 13, 1973

[21] Appl. No.: 396,853

[30] Foreign Application Priority Data
Sept. 26, 1972  Germany............................ 2247095

[52] U.S. Cl. .............................................. 356/136
[51] Int. Cl.² ........................................ G01N 21/46
[58] Field of Search ........... 356/128, 129, 130, 131, 356/132, 133, 134, 135, 136, 137; 250/574

[56] References Cited
UNITED STATES PATENTS

| | | | |
|---|---|---|---|
| 3,311,014 | 3/1967 | Witt et al............................ | 356/133 |
| 3,362,224 | 1/1968 | Melone............................... | 356/133 |
| 3,520,619 | 7/1970 | Ward.................................. | 356/133 |

*Primary Examiner*—John K. Corbin
*Assistant Examiner*—Conrad Clark
*Attorney, Agent, or Firm*—Otto John Munz

[57] ABSTRACT

An apparatus for continuous measurements of the density of variegated liquids, utilizing the angular displacement of the limiting angle at total reflection. Among other purposes the apparatus is useful for measurements of the acid concentration of liquids, such as in a storage battery in a motor vehicle to determine the state of charge of the battery. The apparatus comprises a light rod, in which the end to be immersed in the liquid is provided with a measuring surface and preferably also with a deflecting surface, a light source emitting a bundle of rays into the rod toward the measuring surface at a given divergent angle and a light-sensitive element positioned in the path of rays.

1 Claim, 3 Drawing Figures

APPARATUS FOR MEASURING THE DENSITY OF A CONTAINED LIQUID, BY UTILIZING THE ANGULAR DISPLACEMENT OF THE LIMITING ANGLE AT TOTAL REFLECTION

BACKGROUND OF THE INVENTION

Field of the Invention

An apparatus for measuring the density of a contained fluid mediium by utilizing the angulâr displacement of the limiting angle of rays at total reflection, comprising a bundle of diverging rays, produced by a diaphragm; a light measuring surface, a reflecting surface and a light detector, whereby the bundle of rays is transmitted internally through the fluid as the refractive medium upon the measuring surface and from there is reflected on the deflecting surface and into the detector.

The apparatus is developed as an integral unit with a light transmitting rod.

Description of the Prior Art

The prior art is represented by U.S. Pat. No. 2,483,102 to R. M. Pierson of Sept. 27, 1949 for "Refractometer Employing Photosensitive Devices And Use Of the Same", and U.S. Pat. No. 2,569,127 to G. C. Eltenton of Sept. 25, 1951 for "Refractive Index Meausrement Of Fluids".

For measuring the density of a liiquid, an apparatus with a glass rod immersed in the liquid to be measured already is known. In such an apparatus a light source is provided at the end of the rod that projects from the liquid for producing a pencil of rays entering parallel to the optical axis of the glass rod. On the immersed end of the rod are provided two deflecting surfaces and one measuring surface. The deflecting and measuring surfaces are arranged in such a way that the pencil of rays is transmitted from one deflecting surface to the measuring surface at the angle of total reflection, therefrom to the other deflecting surface and subsequently to a telescope. Such an apparatus is deficient in that the density of the liquid can be determined within very narrow limits and in a subjective manner only. Thererfore a continuous measurement of the density cannot be carried out by means of this apparatus. This apparatus has the further disadvantage in that a relatively strong light soource must be used for a fully satisfactory measurement. Consequently, this apparatus is not well suited to continuous measurement and especially for measuring the acid concentration of a storage battery in a motor vehicle.

In another apparatus of the prior art, a light conductive rod is provided, having one end immersed in the liquid. The immersed end of the rod has a front surface perpendicular to the axis of the rod and is provided with a reflecting coat. The end of the rod that projects from the liquid is provided with a light source and a light-sensitive element. In this apparatus the light rays entering the light-conductive rod are refracted more or less strongly into the liquid dependent on the density of the liquid, so that the amount of light absorbed by the liquid is a criterion for the density of the liquid. It is possible to provide continuous measurement with such an apparatus. However, the depth of the immersion of the light-conductive rod must be always the same. Otherwise substantial errors of measurement might result. The liquid level varies considerably, especially in storage batteries, so that this apparatus cannot be used for measuring the acid concentration of a storage battery.

An apparatus for measuring the acid concentration of a storage battery also is known, having a light source transmitting a pencil of rays directed through a prism filled with the liquid toward several photosensitive receivers. Depending on the density of the liquid, the pencil of rays is more or less strongly refracted by the prism and therefore, depending on the prevailing refractive index, strikes a light sensitive receiver corresponding to this refractive index. Such an apparatus has the shortcoming that it is so large in volume that it cannot be inserted into the storage battery without substantial altertions. Furthermore, this apparatus has a complex structure and is therefore expensive.

SUMMARY OF THE INVENTION

The primary object of the invention is to overcome the difficulties and disadvantages of the prior art.

Another object of the invention is to provide an apparatus which permtis not only a continuous measurement of the density of a liquid, independently of the prevailing liquid level, but also has a simple structure of small volume, is inexpensive and requires only a small power consumption.

Other objects and many of the advantages of the invention will become obvious to those skilled in the art from the following specification in conjunction with the appended drawings.

BRIEF DESCRIPTION OF THE DRAWINGS

The same reference numerals denote the same or equivalent parts throughout the specification and drawings.

DESCRIPTION OF THE PREFERRED EMBODIMENTS

Figure 1:
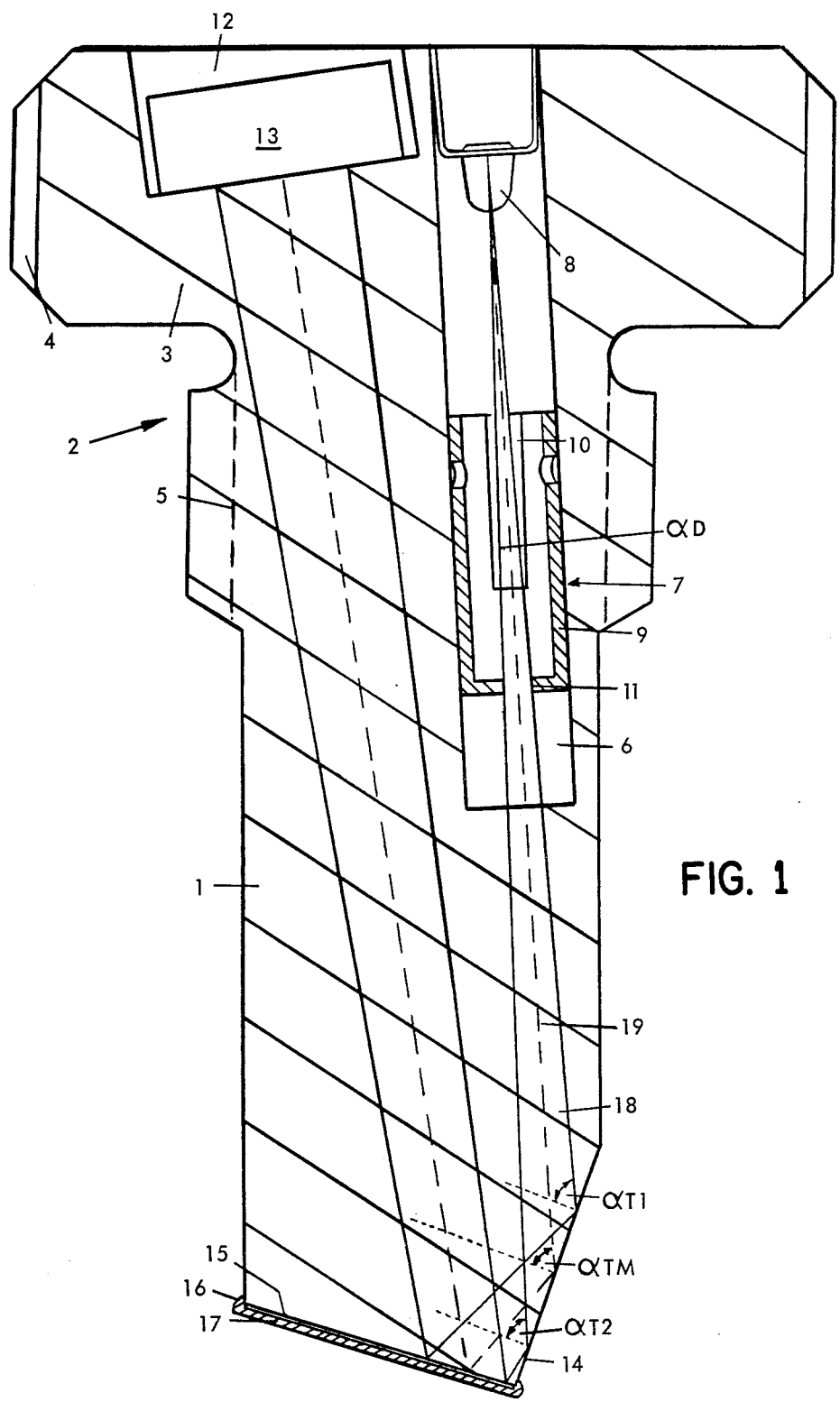
FIG. 1 is a vertical cross sectional view, partially diagrammatical through a first embodiment of the apparatus for measuring density of a liquid, for purposes such as ascertaining the acid concentration of a storage battery.

According to the invention, the deficiencies of the prior art are avoided by providing a device in which a pencil of rays diverges, at least within the range of the measuring surface, by a total angle which equals at least the difference between the total reflection angles at the occuring maximum and minimum liquid densities and which is directed, immediately or via a deflection surface, toward the measuring surface. A line perpendicular to this surface and the longitudinal axis of the pencil of rays enclose an angle which equals the total reflection angle at an average value of liquid density.

By directing a diverging pencil of rays upon the measuring surface and by arranging the measuring surface, with respect to the longitudinal axis of the pencil of rays, as provided by the invention, the following result is achieved: at varying density and thus at a varying refractive index of the liquid, in each instance that portion of the light striking the measuring surface whose angle of incidence with respect to a line perpendicular to the measuring surface exceeds the total reflection angle is refracted into the liquid, while the remaining portion of the light is reflected on the measuring surface and is conveyed, via a deflecting surface, to the photosensitive element. This means that the liquid density can be measured continuously between its occurring maximum and minimum value. Also, the apparatus permits the employment of a relatively weak light source. This is because, elements of very high photosensitivity can be used as receivers and because the light rays are deflected only twice and not three times as in the known apparatus, and therefore the light losses are smaller. Since the measurement of the density of the liquid takes place exclusively at the measuring surface, a suitable choice of the rod length makes it possible, even at varying liquid level for the measuring surface always to be positioned below the minimum light level, whereby variations of the liquid level do not affect the measurements.

The diverging light pencil of rays is most suitably produced by a diaphragm arranged between the light source and the measuring surface. For precise and easy setting of the required angle of divergence, the diaphragm is advantageously displaceable parallel to the longitudinal axis of the pencil rays. Instead of a diaphragm, or also in combination therewith, a condenser lens may be mounted between the light source and the measuring surface. This condenser lens furnishes a higher light yield than a diaphragm but is somewhat more expensive. Which of the two structural elements is preferable depends on the requirements of the apparatus.

The deflecting surface on which the portion of light which arrives from the measuring surface is reflected toward the photosensitive element, when the pencil of rays emanating from the light source is directed immediately toward the measuring surface, preferably is a plane for reasons of efficient manufacture. It is, however, also possible to shape the deflecting to be parabolically curved if, for reasons of construction, focusing of the pencil of rays should be necessary. Such a parabolically curved deflecting surface is advantageous, especially when a condenser lens is provided, since the light yield can thereby be further increased. In order to improve the reflection properties of the deflecting surface, it is advisable to provide the latter with a reflecting layer and to cover the layer with a protective coat which is not attacked by the liquid. In an apparatus for measuring the acid concentration of a storage battery, bitumen, for instance, can be used as the protective coat. Conventional materials such as silver, aluminum, or gold may be used as the reflecting layer. A gold layer has proved particularly advantageous, especially in connection with a gallium arsenide diode as the light source — the latter being excellently suitable for the present purposes on account of its volume and its small power consumption — or with an incandescent lamp operated at low-tension voltage because with relation to the spectrum of the light emanating from such a light source, the gold layer exhibits an extremely high degree of reflection.

In an embodiment preferred for the measurement of the acid concentration of a storage battery, the light conductive rod is mounted, with the end remote from the measuring surface, on a battery closure plug and the light source and the photosensitive element are arranged in its head. Such a structure of the apparatus requires neither structural changes in the battery casing nor additional means for fastening the apparatus to the battery casing. This results in the advantage that the mounting of the apparatus on the battery casing can be carried out by untrained personnel and therefore also by the driver of the vehicle. The embodiment of the apparatus described is therefore excellently suited for supplemental equipment for storage batteries already mounted in the motor vehicle.

Figure 2:
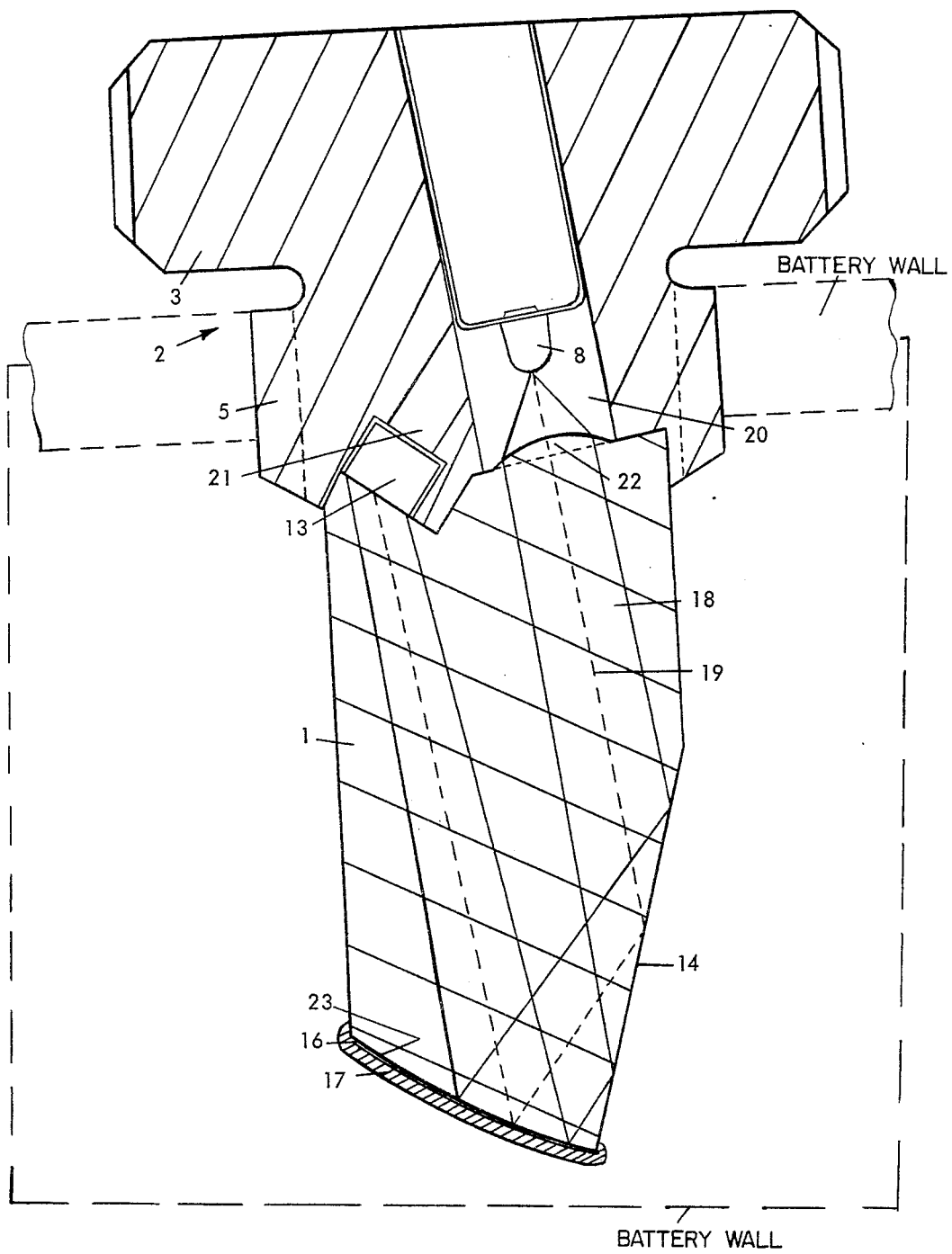
FIG. 2 is a similar view modified with relation to the apparatus of FIG. 1.

The fastening of the light conductive rod on the closure plug can be carried out by means of a screw or plug connection. When a screw connection is provided, the rod may be provided with an outside screw thread on the side facing away from the measuring surface, and the closure plug may be provided with a corresponding inside screw thread. It has, however, proved particularly practical to construct the light conductive rod and the battery closure plug as a one-piece plastic unit. This results in substantial advantages with respect to the manufacture of the apparatus, since such a structural part can be manufactured in a single working operation by an injection-molding or pressing process. Especially in an embodiment such as is depicted in FIG. 2, the diaphragm, for reasons of efficient manufacture, advantageously has a casing which is provided at one end with at least two longitudinal slots and is closed at the other end, leaving a diaphragm opening uncovered. The casing is held in a bore passing through the plug and possibly the rod portion, supporting itself therein resiliently with its slotted end. The casing serving as the diaphragm can be manufactured in an extrusion and punching process and the bore can be molded therein during the manufacturing process of the plug or the plug-and-rod unit. When, instead of a diaphragm or in combination therewith, a condenser lens is used, the latter advantageously forms a one-part unit with the light conductive rod.

The position of the light source and the photosensitive element with respect to each other and to the photoconductive rod may itself be selected almost arbitrarily since the position of the measuring surface and the deflecting surface can be adapted within wide limits to the arrangement selected. under certain conditions, however, it is advantageous with respect to the mechanical loading capacity of the plug element to produce the device in such a manner that the longitudinal axis of the pencil of rays and the longitudinal rod axis enclose an acute angle, which preferably equals approximately the angle of divergence of the pencil of rays. This is particularly advantageous when a case-shaped diaphragm is used and the bore holding the diaphragm is relatively long.

The concentration of the acid in a storage battery depends, as is known, on the temperature, i.e. it decreases at a rising temperature. Since, however, the viscosity of the acid likewise decreases at a rising temperature and this effect outweighs the other one, it is possible at higher temperature to put a heavier load on the battery, notwithstanding the decreasing concentration. This dependence can, according to a further concept of the invention, be taken into consideration by arranging a thermometer probe on or in the portion of the light-conductive rod immersed in the liquid and feeding the output signal of this thermometer probe as a correction value into the indicating current circuit.

The apparatus of FIG. 1 comprises a light conductive rod 1 which at one end changes over to an element 2 optionally shaped as a battery closure plug and forms therewith a one-part unit made of polymethyl methacrylate. The closure plug element 2 comprises a head 3 whose periphery is provided with a milled edge 4, and a thread section 5.

A bore 6 is provided with a diaphragm 7. In the opening of the bore, a gallium arsenide diode 8 is inserted, serving as a light source. The bore extends through the closure plug element 2 and a portion of the rod 1. The diaphragm 7 is constructed as a casing 9, provided with three longitudinal slots 10, displaced by about 120 angle degrees. Only one of the slots is visible. The slot is closed at the lower unslotted end, leaving a diaphragm aperture 11 open. The casing 9 is supported, by way of its parts separated through the slots 10 on the inner wall of the bore 6 and is therefore held, displacably, in the direction of the longitudinal axis, in the bore 6. In the battery closure plug element 2, a recess 12 is provided in which is mounted a photoconductive cell 13 serving as the photoconductive element. It is inserted, either directly or through an operational amplifier, in a current indicating circuit.

At the free end of the photoconductive rod 1 there is the measuring surface 14 and a plane deflecting surface 15 to which a gold layer 16 and a protective cover 17 of bitumen is applied. The light produced by the gallium arsenide diode 8 is formed, in cooperation with the diaphragm 7, into a pencil of rays 18 which diverge with an angle which equals the difference of the total reflection angles at the maximum and minimum occurring acid concentration. In the present case the density limiting values are prespecified by the limiting states of the charge of the storage battery. The acid concentration of a lead storage battery used as starter battery as designed for Central Europe in a charged state is about 1.28 kg/l and in a discharged state about 1.18 kg/l. A refractive index of the acid of about 1.380 or 1.364, respectively, corresponds to these values, and at a refractive index of the light conductive polymethyl methacrylate rod 1 of 1.49, the total reflection angle is $\alpha T_1$ or $\alpha T_2$, respectively, of approximately 67.85 and 66.26 angle degrees, respectively.

The pencil of rays 18 diverges therefore with an angle $\alpha D$ of about 1.6 degrees. The pencil of rays 18 is directed immediately toward the measuring surface 14. A line perpendicular to the measuring surface and the longitudinal axis 19 of pencil rays 18 enclose an angle $\alpha TM$ of about 67 degrees. This angle equals the total reflection angle at an average value of density of the liquid. The aforementioned values apply at a temperature of about 20°C. The pencil of rays 18 is reflected from the measuring surface 14, according to the density of the acid, entirely or partially toward the deflecting surface 15 and therefrom toward the photoconductive cell 13, which consequently is illuminated in accordance with the acid concentration and therefore the state of charge. The inclination of the deflecting surface 15 can be calculated, when the inclination of the measuring surface 14 and the approximate position of the photoconductive cell 13 are known, by means of simple geometrical relations. For reasons already mentioned, the longitudinal axis 18 does not extend parallel to the rod axis but at an acute angle therewith which corresponds approximately to the angle of divergence of the pencil of rays 18. The temperature thermometer probe is arranged in a bore extending in the direction of the longitudinal axis and passing through the plug element 2 and a portion of rod 1, but is not shown for the sake of clarity.

The apparatus of FIG. 2 contains likewise a light conductive rod 1 which is fastened at one end to element 2 constructed as a battery closure plug, by means of screws not shown. Rod 1 is made of polymethyl methacrylate, and the plug element 2 of a material customarily employed for such an element. The plug element 2 has two bores 20 and 21 wherein light source 8 and the photosensitive element 13 are arranged respectively. A condensor lens 22 is molded on the side of rod 1 that faces the light source 8. The pencil of rays 18 is formed through the condensor lens. A measuring surface 14 and a parabolically curved deflecting surface 23 are provided at the free end of rod 1. Such an apparatus has an entwined path of rays. The angle of divergence of the pencil of rays and the angle between a line perpendicular to the measuring surface and the axis of the pencil of rays 19 correspond to the above values since the apparatus is intended for the same purpose as the aforementioned one. In such an apparatus, the light yield, as already mentioned, is particularly great.

Figure 3:
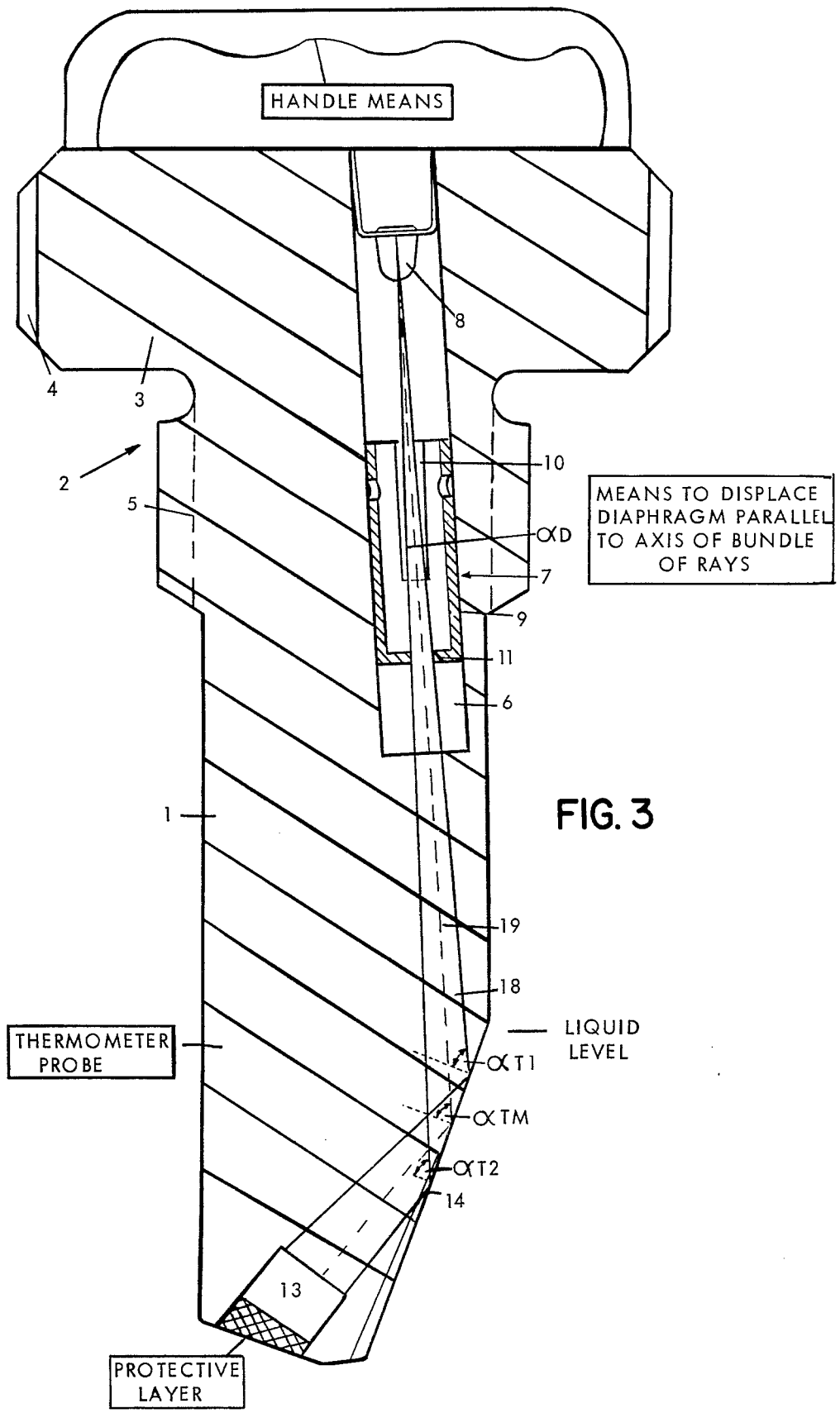
FIG. 3 is a view similar to that of FIGS. 1 and 2 avoiding the use of a deflecting surface.

The apparatus of FIG. 3, while similar to those illustrated in FIGS. 1 and 2, is devoid of the reflecting surface, the battery plug and the shaft.

It shows the protective layer in the bottom. The electric circuit connection for the detector 13 is mounted from the top to protect it from corrosion by the acid.

The apparatus of the invention may be constructed as a portable rod-device, usable at various occasions on a variety of containers and with variegated fluids.

Its function will remain unaffected by the direction at which the rod is inserted into the liquid, which may be perpendicular, horizontal, at an angle thereto, from above, from the side or from the bottom, as long as the measuring surface is immersed into the liquid.

Thus the apparatus has a usefulness and purpose independent from any container.

In specific embodiments, such as in combination with a car battery, it has of course an additional usefulness, providing immediate means to ascertain promptly the density of the liquid and/or the acidity of the battery liquid.

What is claimed is:

1. An apparatus for measuring the density of a liquid by using the angular displacement of the limiting angle at total reflection comprising
   A. an elongated light transducing rod,
   B. a measuring surface limited to one end of said rod, wherein, in operation, the measuring surface is immersed into said liquid,
   C. light source means for emitting a bundle of rays into the other end of the rod and directed to strike the measuring surface, the bundle of rays diverging on the measuring surface at a total divergent angle which is at least equal to the difference between the total reflection angles of the surface when respectively immersed into said liquid at its maximum and minimum densities within a range of densities to be measured by the apparatus, the bundle of rays being directed toward the measuring surface such that a longitudinal axis formed by the bundle of rays forms with a line perpendicular to the measuring surface an angle which is approximately equal to the total reflection angle of the measuring surface when it is immersed into a sample of said liquid having an average value of density within said range of densities to be measured,
   D. a light detector on said other end of said rod responsive to the rays of said bundle of rays,
   E. a light reflecting surface limited to said one end of said rod and placed to receive the rays which have been reflected by the measuring surface and to reflect the received rays to the light detector, F. a battery closure plug on said rod at said other end of the rod remote from said one end of said rod, whereby said measuring surface reflects a portion of the beam which varies with the density of said liquid, said portion being again reflected by the reflecting surface to strike the light detector, the amount of light striking the light detector being a function of the density of the liquid, G. a diaphragm provided between the light source and the measuring surface, and H. means to displace the diaphragm along an axis parallel to the axis of the bundle of rays.

* * * * *

UNITED STATES PATENT OFFICE
CERTIFICATE OF CORRECTION

Patent No. 3,977,790　　　　　　　　　Dated　August 31, 1976

Inventor(s)　Walter Schweizer et al.

It is certified that error appears in the above-identified patent and that said Letters Patent are hereby corrected as shown below:

On the Title Page name of Co-Inventor should read

-- Martin-Ulrich Reissland --.

Signed and Sealed this

Eighteenth Day of October 1977

[SEAL]

Attest:

RUTH C. MASON　　　　　　　　LUTRELLE F. PARKER
Attesting Officer　　　　Acting Commissioner of Patents and Trademarks